(12) United States Patent
Fishman et al.

(10) Patent No.: US 6,638,914 B1
(45) Date of Patent: *Oct. 28, 2003

(54) PHARMACEUTICAL ADMINISTRATION OF ADENOSINE AGONISTS

(75) Inventors: Pnina Fishman, Herzliya (IL); Ilan Cohn, Herzliya (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,744

(22) PCT Filed: Jan. 7, 2000

(86) PCT No.: PCT/IL00/00014

§ 371 (c)(1),
(2), (4) Date: Jan. 9, 2001

(87) PCT Pub. No.: WO00/40251

PCT Pub. Date: Jul. 13, 2000

(30) Foreign Application Priority Data

Jan. 7, 1999 (IL) .................................................. 127947

(51) Int. Cl.$^7$ .............................................. A61K 31/70
(52) U.S. Cl. .......................................... 514/46; 514/81
(58) Field of Search ..................................... 514/46, 81

(56) References Cited

U.S. PATENT DOCUMENTS

| | | | |
|---|---|---|---|
| 4,791,103 A | | 12/1988 | Trivedi et al. ................. 514/46 |
| 5,498,605 A | | 3/1996 | Jacobson et al. .............. 514/46 |
| 5,686,114 A | * | 11/1997 | Welsh ........................ 424/601 |
| 5,882,927 A | * | 3/1999 | Bennett et al. .............. 435/375 |
| 5,958,907 A | * | 9/1999 | Welsh ........................ 514/108 |
| 5,998,387 A | | 12/1999 | Belardinelli et al. .......... 514/46 |
| 5,998,388 A | | 12/1999 | Ellis et al. ..................... 514/46 |
| 2001/0031742 A1 | * | 10/2001 | Fishman et al. .............. 514/45 |
| 2002/0037871 A1 | * | 3/2002 | Fishman et al. .............. 514/46 |

FOREIGN PATENT DOCUMENTS

| | | |
|---|---|---|
| WO | 9402497 | 2/1994 |
| WO | 9724363 | 7/1997 |
| WO | 9743300 | 11/1997 |
| WO | WO9808855 | 3/1998 |
| WO | WO 9902143 | 1/1999 |
| WO | WO0071558 | 11/2000 |
| WO | WO 0107060 A1 | 2/2001 |
| WO | WO 02/09701 A1 * | 7/2002 |

OTHER PUBLICATIONS

Fishman et al. (III), "Extracellular Adenosine Acts as a Chemoprotective Agent," *Proc. American Association for Cancer Research*, 39, 470 (Mar., 1996.).*

Siddik et al., "Metabolism of New Anticancer Agents," *Pharmacology & Therapeutics*, 41(1+2), 163–194 (1989). Month of publication data is unavailable.*

Williams, "Adenosine Receptors—An Historical Perspective," Chapter 1 in *Adenosine and Adenosine Receptors*, M. Williams (ed)., The Humana Press, Clifton, NJ, 1990, only pp. 1–15 supplied.*

Trivedi et al., Structure–Activity Relationships of Adenosine $A_1$ and $A_2$ Receptors, Chapter 3 in *Adenosine and Adenosine Receptors*, M. Williams (ed.), The Humana Press, Clifton, NJ, 1990, only pp. 57–103 supplied. Month of publication data is unavailable.*

Cooper et al., "Signal Transduction Mechanisms for Adenosine," Chapter 4 in *Adenosine and Adenosine Receptors*, M. Williams (ed.), The Humana Press, Clifton, NJ, 1990, only pp. 105–141 supplied. Month of publication data is unavailable.*

Cronstein et al., "Adenosine and Host Defense," Chapter 12 in *Adenosine and Adenosine Receptors*, M. Williams (ed.), The Humana Press, Clifton, NJ 1990, only pp. 475–500 supplied. Month of publication data is unavailable.*

Meininger et al., "Role of Adenosine in Angiogenesis," Chapter 19 in *Adenosine and Adenine Nucleotides as Regulators of Cellular Function*, J. W. Phillis (ed.), CRC Press, Boca Raton, FL, 1991, only pp. 241–246 supplied. Month of publication data is unavailable.*

Hirano et al., "Functional Coupling of Adenosine $A_{2a}$ Receptor Inhibition of the Mitogen–Activated Protein Kinase Cascade in Chinese Hamster Ovary Cells," *Biochemical Journal*, 316(Pt. 1), 81–86 (May 15, 1996). Month of publication data is unavailable.*

Boyd et al., "The Neutralization of Aminopterin–Induced Leukopenia by Adenosine–5–phosphoric Acid," *Journal of Laboratory and Clinical Medicine*, 41, 931–935 (1953); *Chemical Abstracts*, 47(19), Abstract No. 10116c–e (Oct. 10, 1953); CAPlus cite is "1953: 59519.".*

(List continued on next page.)

*Primary Examiner*—James O. Wilson
*Assistant Examiner*—L E Crane
(74) *Attorney, Agent, or Firm*—Browdy and Neimark, P.L.L.C.

(57) ABSTRACT

The present invention relates to pharmaceutical compositions for use in inducing proliferation of the hematopoietic system, in particular, of bone marrow cells, comprising a pharmaceutically acceptable carrier, excipient or diluent and, as an active ingredient, an effective amount of an adenosine A1 receptor agonist. The pharmaceutical composition of the present invention may be used to induce proliferation of bone marrow cells, in a variety of clinical situations where such proliferation is therapeutically beneficial.

The active ingredient within the pharmaceutical composition of the invention may be a compound of general formula (I) as described herein or any other compound or substance which specifically binds to and/or activates the A1 adenosine receptor and acts as an agonist to the receptor's natural ligand.

14 Claims, 1 Drawing Sheet

OTHER PUBLICATIONS

Matsumoto et al., "Nucleoside–Nucleotide Mixture Increases Peripheral Neutrophils in Cyclophosphoramide–Induced Neutropenic Mice," *Nutrition* 11(3), 296–299 (May/Jun., 1995); *Chemical Abstracts,* 123(19), pp. 1043–1044, Abtract No. 255501q (Nov. 6, 1995).*

Fukunaga et al., "Hypotensive Effects of Adenosine and Adrenosine Triphosphate Compared with Sodium Nitroprusside," *Anesthesia and Anaglesia,* 61(3), 273–278 (Mar., 1982).*

Collis, M. G., "The Vasodilator Role of Adenosine," *Pharmacology and Therapeutics,* 41(½), 143–162 (1989).*

Epstein et al., "Protection of Normal Hematopoietic Stem Cells From the Toxicity of Purine Base Analogs: In Vivo Application," *Cancer Treatment Reports,* 68(9), 1153–1156, (Sep., 1984). Month of publication is unavailable.*

Hoon–Eng Khoo et al., "Differential Expression of Adenosine A1 Receptors in Colorectal Cancer and Related Mucosa", Cancer Letters, 106, pp. 17–21, 1996.

Pnina Fishman et al., "Adenosine and Other Low Molecular Weight Factors Released by Muscle Cells Inhibit Tumor Cell Growth", Cancer Research, 58, pp. 3181–3187, Jul. 15, 1998.

John W. Daly, "Adenosine Receptors: Targets for Future Drugs", *Journal of Medicinal Chemistry,* Mar. 1982, vol. 25, No. 3, pp. 197–207.

Snowdy et al., *British J. Pharmacol.,* 126:137–146 (1999. Month of publication is unavailable for this reference.

Jacobson et al., "Functionalized Congeners of Adenosine . . . ", *Journal of Medicinal Chemistry,* 1985, vol. 28, No. 9, pp. 1341–1346. Month of publication is unavailable for this reference.

Michael G. Collis, "The Vasodilator Role of Adenosine", *Pharmac. Ther.,* 1989, vol. 41, pp. 143–162. Month of publication is unavailable for this reference.

Williams, Drug Development Research, vol. 28, No. 3, pp. 438–444 (1993). Month of publication is unavailable for this reference.

Moos et al., Journal of Medicinal Chemistry, vol. 28, No. 10, pp. 1383–1384 (Oct., 1985).

Tey et al., Biochemical and Biophysical Research Communications, vol. 187, No. 3, pp. 1486–1492 (Sep. 30, 1992).

* cited by examiner

PHARMACEUTICAL ADMINISTRATION OF ADENOSINE AGONISTS

This application is the national phase under 35 U.S.C. §371 of PCT International Application No. PCT/IL00/00014 which has an International filing date of Jan. 7, 2000, which designated the United States of America.

FIELD OF THE INVENTION

This invention relates to drugs for use in cancer therapy. More specifically, the present invention concerns drugs which induce proliferation of cells of the hematopoietic system.

PRIOR ART

The following is a list of prior art references considered to be relevant as background to the invention:

1. Daly, J. W., Adenosine receptors: Targets for future drugs. *J. Med. Chem.*, 25:197–207, 1982.
2. Stiles, G. L., Adenosine receptors and beyond: Molecular mechanisms of physiological regulation, *Clin. Res.*, 38:10–18, 1990.
3. Collis, M. G., The vasodilator role of adenosine, *Pharmacol. Ther*, 41:143–162, 1989.
4. Fishman et al., Extracellular adenosine acts as a chemoprotective agent, *Proceeding of the American Association for Cancer Research*, 39:470, 1998.
5. Moos, W. H., et al., $N^6$-cycloalkyladenosines. Potent $A_1$ selective adenosine agonists, *J. Medicinal Chemistry* 28:1383–1384, 1985.
6. Jacobson, K. A et al., Functionalized congeners of adenosine, *J. Medicinal Chemistry* 28:1341–1346, 1985.
7. U.S. Pat. No. 5,998,387.
8. U.S. Pat. No. 5,998,388
9. U.S. Pat. No. 5,498,605.
10. U.S. Pat. No. 4,791,103.

BACKGROUND OF THE INVENTION

Adenosine is an extracellular messenger generated by all cells in the body. It is known to regulate different physiological processes within cells through binding to specific cell surface receptors—$A_1$ and $A_2$ receptors[1, 2, 3]. It was recently demonstrated that adenosine inhibits proliferation of tumor cells and induces proliferation of bone marrow cells[4]. Further more it was also shown that adenosine can protect white blood cells, particularly neutrophils, from destruction which is otherwise caused by chemotherapeutic drugs[4].

SUMMARY OF THE INVENTION

The present invention is based on the surprising findings that (i) the effect of adenosine in inducing proliferation of bone marrow cells can be inhibited by $A_1$ receptor antagonists (antagonist that inhibits binding of adenosine to adenosine $A_1$ receptor), and (ii) the effect of adenosine can be mimicked by an adenosine $A_1$ receptor agonist ("$A_1$RAg"). These findings led to the conclusion that the bone marrow proliferation-induction effect of adenosine is mediated, at least to some extent through the $A_1$ receptor, and that accordingly $A_1$RAg may be used to induce proliferation of bone marrow cells, in a wide variety of clinical situations where such proliferation is therapeutically beneficial.

The present invention provides, by a first of its aspects, a pharmaceutical composition for use in inducing proliferation of bone marrow cells, comprising a pharmaceutically acceptable carrier, excipient or diluent and, as an active ingredient, an effective amount of an $A_1$RAg.

The present invention provides, by a second of its aspects, use of an $A_1$RAg for the production of a pharmaceutical composition for use in inducing proliferation of bone marrow cells.

The present invention further provides a method of inducing proliferation of bone marrow cells in a subject, comprising administering to the subject an effective amount of an A1RAg.

The term "effective amount" used above and below should be understood as meaning an amount of an A1RAg which is capable of achieving a desired therapeutic effect, particularly, in inducing proliferation of bone marrow cells. The desired therapeutic effect depends on the type and mode of treatment. When, for example, said A1RAg is administered to counter drug-induced leukopenia, an effective amount thereof may be an amount which protects the treated subject against the drug-induced reduction in the count of leukocytes, particularly neutrophils; an amount of the active ingredient which can give rise to an increase in an already decreased level of such cells, e.g. restore the level to a normal level or sometimes even above; etc. The man of the art will have no difficulties, on the basis of a limited number of routine experiments, to determine an effective amount in each case.

As will be appreciated, the effective amount may also depend on the treated subject's gender, on the individual's weight, on the therapeutic regime, namely whether the $A_1$RAg is administered once daily, several times daily, once in several days, etc. Furthermore, the effective amount may depend on the exact nature or etiology of the disease or condition which is being treated or intended to be prevented.

According to one embodiment of the invention, the $A_1$RAg are adenosine derivatives carrying at least an $N^6$-substituent. Other positions may also be substituted. In fact, it has been found that the biological activity of an adenosine derivative may be enhanced by modifying other parts of the nucleotide, for example, at the 2- and/or 5' positions (e.g. with chloro atoms). Such substituents were found to increase the molecule's $A_1$ selectivity.

The adenosine derivatives which can be used according to the present invention are generally defined by the following formula (I):

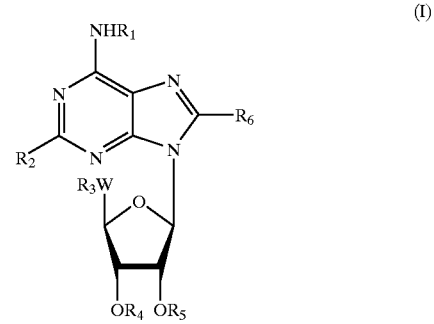

(I)

wherein $R_1$ represents a lower alkyl, cycloalkyl, preferably $C_3$–$C_8$ cycloalkyl (including the well known cyclohexyl and cyclopentyl containing derivatives, recogrlzed as CPA and CHA, respectively), the cycloalkyl group may be substituted with, for example, a hydroxyl or lower allyl; $R_1$ also represents a hydroxyl or hydroxyalkyl; a phenyl, anilide, or lower alkyl phenyl, all optionally substituted by one or more substituents, for example, halogen, lower allyl, haloalkyl such as trifluoromethyl, nitro, cyano, —$(CH_2)_mCO_2R^a$, —$(CH_2)_mCONR_2R^aR^b$, —$(CH_2)_mCOR^a$, m representing an integer from 0 to 6; —$SOR^c$, —$SO_2R^c$, —$SO_3H$, —$SO_2NR^aR^b$, —$OR^a$, —$SR^a$, —$NHSO_2R^c$, —$NHCOR^a$, —$NR^aR^b$ or —$NHR^aCO_2R^b$; wherein $R^a$ and $R^b$ represent independently a hydrogen, lower alkyl, alkanoyl, phenyl or naphthyl (the latter may be partially saturated) the alkyl group optionally being substituted with a substituted or unsubsituted phenyl or phenoxy group; or when $R_1$ represents —$NR^aR^b$, said $R^a$ and $R^b$ form together with the nitrogen atom a 5- or 6- memebered heterocyclic ring optionally containing a second heteroatom selected from oxygen or nitrogen, which second nitrogen heteroatom may optionally be further substituted by hydrogen or lower alkyl; or —$NR^aR^b$ is a group of general formulae (II) or (III):

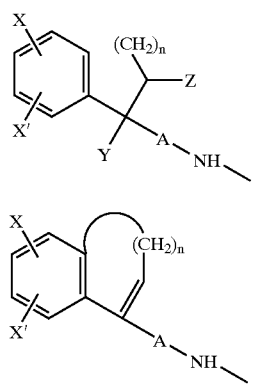

wherein
n is an integer from 1 to 4;
Z is hydrogen, lower alkyl or hydroxyl;
Y is hydrogen, lower alkyl, or OR' where R' is hydrogen, lower alkyl or lower alkanoyl;
A is a bond or a lower alkylene, preferably, $C_1$–$C_4$ alkenyl; and
X and X' are each independently hydrogen, lower alkyl, lower alkoxy, hydroxy, lower alkanoyl, nitro, haloalkyl such as trifluoromethyl, halogen, amino, mono- or di-lower alkyl amino, or when X and X' are taken together a methylenedioxy group;
$R^c$ represents a lower alkyl;
$R_2$ represents a hydrogen; halogen; substituted or unsubsituted lower alkyl or alkenyl group; lower haloalkyl or haloalkenyl; cyano; acetoamido; lower alkoxy; lower alkylamino; $NR^dR^e$ where $R^d$ and $R^e$ are independently hydrogen, lower alkyl, phenyl or phenyl substituted by lower alkyl, lower alkoxy, halogen or haloalkyl such as trifluoromethyl or alkoxyl; or —$SR^f$ where $R^f$ is hydrogen, lower alkyl, lower alkanoyl, benzoyl or phenyl;
W represents the group —$OCH_2$—, —$NHCH_2$—, —$SCH_2$— or —$NH(C=O)$—;
$R_3$, $R_4$ and $R_5$ represent independently a hydrogen, lower alkyl or lower alkenyl, branched or unbranched $C_1$–$C_{12}$ alkanoyl, benzoyl or benzoyl substituted by lower alkyl, lower alkoxy, halogen, or $R_4$ and $R_5$ form together a five membered ring optionally substituted by a lower alkyl or alkenyl; $R_3$ further represents independently a phosphate, hydrogen or dihydrogen phosphate, or an alkali metal or ammonium or dialkali or diammonium said thereof;

$R_6$ represents a hydrogen, halogen atom; or
one of the R groups (i.e. $R_1$ to $R_6$) is a sulfohydrocarbon radical of the formula $R^g$—$SO_3$—$R^h$—, wherein $R^g$ represents a group selected from $C_1$–$C_{10}$ aliphatic, phenyl and lower alkyl substituted aromatic group which may be substituted or unsubstituted and $R^h$ represents a monovalent cation. Suitable monovalent cations include lithium, sodium, potassium, ammonium or trialkyl ammonium, which will enable dissociation to take place under physiological conditions. The remaining R groups being a hydrogen or halogen atom, an unsubstituted hydrocarbon or any other non-sulfuir containing group as defined above.

The active ingredient may be as defined above or in the form of salts or solvates thereof, in particular physiologically acceptable salts and solvates thereof. Further, when containing one or more asymmetric carbon atoms, the active ingredient may include isomers and diastereoisomers of the compounds of formula (I) and mixtures thereof.

The hydrocarbon chains used herein may include straight or branched chains. In particular, the terms "alkyl" or "alkenyl" as used herein mean a straight or branched chain alkyl or alkenyl groups.

The terms "lower alkyl or lower alkenyl" mean respectively $C_1$–$C_{10}$ alkyl or $C_2$–$C_{10}$ alkenyl groups and preferably, $C_1$–$C_6$ alkyl and $C_2$–$C_6$ alkenyl groups.

Pharmaceutically acceptable salts of the compound of general formula (I) include those derived from pharmaceutically acceptable inorganic and organic acids. Examples of suitable acids include hydrochloric, hydrobromic, sulphoric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids.

Preferred adenosine derivatives of formula (I) are the $N^6$-cyclopentyl adenosine (CPA), 2-chloro-CPA (CCPA), and $N^6$-cyclohexyl adenosine (CHA) derivatives, the preparation of which is well known to the person skilled in the art. Other adenosine derivatives which are known to be selective to the $A_1$ receptor are those wherein $R_1$ is a anilide group, the latter may be unsubstituted or substituted for example with hydroxyl, alkyl, alkoxy or with a group —$CH_2C(O)R"$, $R"$ being an hydroxyl group, —$NHCH_3$, —$NHCH_2CO_2C_2H_5$, (ethyl glycinate), tuloidide (also in which the methyl moiety is replaced with a haloalkyl moiety), or with a group —$CH_2C(O)NHC_6H_4CH_2C(O)R'''$, in which R''' represents a group to yield a methyl ester substituent (—$OCH_3$), an amide substituent (e.g. R''' being a group —$NHCH_3$), or R''' being a hydrazide, ethylenediamine, —$NHC_2H_5NHC(O)$ $CH_3$, 4-(hydroxyphenyl) propionyl, biotinylated ethylene diamine or any other suitable hydrocarbon which renders the compound an $A_1$ agonist. The preparation of some of the above specific adenosine derivatives is described in the art[5-8].

Alternatively, the $N^6$-substituted adenosine derivatives used as active ingredients according to the present invention may be those containing an epoxide moiety and more particularly are a cycloalkyl epoxy containing adenosine derivative (e.g. oxabicyclo such as norbomanyl or oxatricyclo such as adamantanyl). Some such compounds may be defined by general formula (I), wherein R$_1$ is a group of general formulae (IVa) and (IVb):

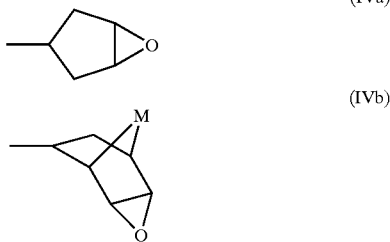

wherein M is a lower alkyl group as defined above.

Embodiments of the agonist compounds having an epoxide N$^6$-norbornyl group include the endo and exo isomers and more particularly, can be one of four isomers: the 2R-exo, 2R-endo, 2S-exo and 2S-endo form.

Another embodiment of the N$^6$-orbornyl derivative may include an oxygen atom at the N$^1$-position of the purine ring. This compound is termed N$^6$-(5,6-epoxynorbom-2-yl) adenosine- 1-oxide.

At times, the active ingredient may be an adenine derivative in which the β-D-ribofuranozyl moiety of adenosine is replaced with a hydrogen or phenyl group.

The invention has a wide range of terapeutic utilities and provides treatment for a wide range of diseases, disorders or conditions in both human and non-human animals, where induction of proliferation of bone marrow cells may be beneficial to the treated subject. Therapeutic applications include immunomodulation in a subject having a weak immune system, for example: as a result of a genetic disorder; as a result of an infection by an infectious agent, e.g. a virus; as a result of a general stress situation, e.g. following a car or another accident, etc.; as a result of a treatment which causes reduction in the level of leukocytes, particularly, neutrophils, e.g. a chemotherapy or treatment with a neuroleptic drug; etc.

A treatment according to the invention may be used to reduce the risk of infection resulting from congenital or acquired neutropenias.

The present invention may also be used for the treatment of subjects having a low count of white blood cells, either a general low count or a count of a specific class of white blood cells, e.g. neutrophils. A weakened immune system manifested by a reduction in white blood cell count, is often seen in cancer patients, and when this occurs, this may have a severe effect on the treated patent, and may at times even be a cause of death. In such a case it is thus important to try and increase the white blood cell count. This may be achieved by the treatment in accordance with the invention.

Reduction of white blood cell count, particularly of neutrophils, is very often an undesired side effect of a variety of treatments, including: anti-cancer therapy by chemotherapy or radiotherapy; treatment of a subject with neuroleptic drugs; etc. The active ingredient of the invention may be used in such subject to counter these undesired side effects of the treatment. In accordance with some therapeutic regimes, the active ingredient of the invention may be administered prior to such treatment, or concurrently therewith. For example, in the case of a treatment with a chemotherapeutic drug or treatment with a neuroleptic drug, the active ingredient of the invention may be administered either prior to the onset of treatment with the chemotherapeutic or the neuroleptic drug during such treatment, or may also at times be given after such treatment. In other words, the active ingredient of the invention may be used eitier as a preventive agent, namely to prevent reduction of the white blood cell level as a result of the treatment, or may be used as an acute therapeutic agent for simulating an increase in the level of the white blood cells after the level was reduced as a result of said treatment.

In accordance with one embodiment of the invention, an anti-cancer chemotherapeutic agent or a neuroleptic drug may be combined in one formulation with the active ingredient of the invention.

BRIEF DESCRIPTION OF THE FIGURES

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

The invention will now be illustrated by the following description of some experiments carried out according thereto.

MATERIALS AND METHODS

Mice Female ICR or C57BL/6J mice aged 3 months, weighing an average of 25 g were used. The mice were purchased from Harlan Laboratories, Jerusalem, Israel. Standardized pelleted diet and tap water were supplied.

Drugs

All drugs were purchased from Sigma Chemical Co. St. Louis, Mo. Adenosine was dissolved in water and kept as a stock solution in a concentration of 1 mM. For in vitro studies, dilutions in RPMI medium were carried out and final concentrations of 100, 50, 25, 10 and 5 μM were used. For in vivo studies, the stock solution was diluted with PBS to a concentration of 3 mM and 0.5 ml was injected intraperitoneally to mice. 1,3-dipropyl-8-cyclopentylxanthine (DPCPX), an adenosine A$_1$ receptor antagonist, 3,7-dimethyl-1-propargyl-xanthine (DMPX) an A$_2$ receptor antagonist and N-cyclopentyladenosine (CPA), a selective A$_1$ receptor agonist were added to a culture of proliferating bone marrow cells.

Evaluation of Bone Marrow Cell Proliferation in vitro

Bone marrow cells were obtained from the femur of C57BL/6J mice. Cells were disaggregated by passing through a 25G needle. [$^3$H]-Thymidine incorporation assay was used to evaluate the proliferative capability of the bone marrow cells.

Cells (3×10$^4$/well) were incubated with RPMI medium, containing 10% fetal calf serum (FCS) (Biological Industries, Beit Haemek, Israel) and adenosine, adenosine antagonists or the agonist in 96 microtiter plates for 48 h. Cultures containing cells were suspended in RPMI medium and 10% FCS served as controls. In the last 6 hours of incubation, each well was pulsed with 1 $\mu$Ci [$^3$H]-thymidine. Cells were harvested and the $^3$[H]-thymidine uptake was determined in an LKB liquid scintillation counter (LKB, Piscataway, N.J. USA).

RESULTS

Figure 1:
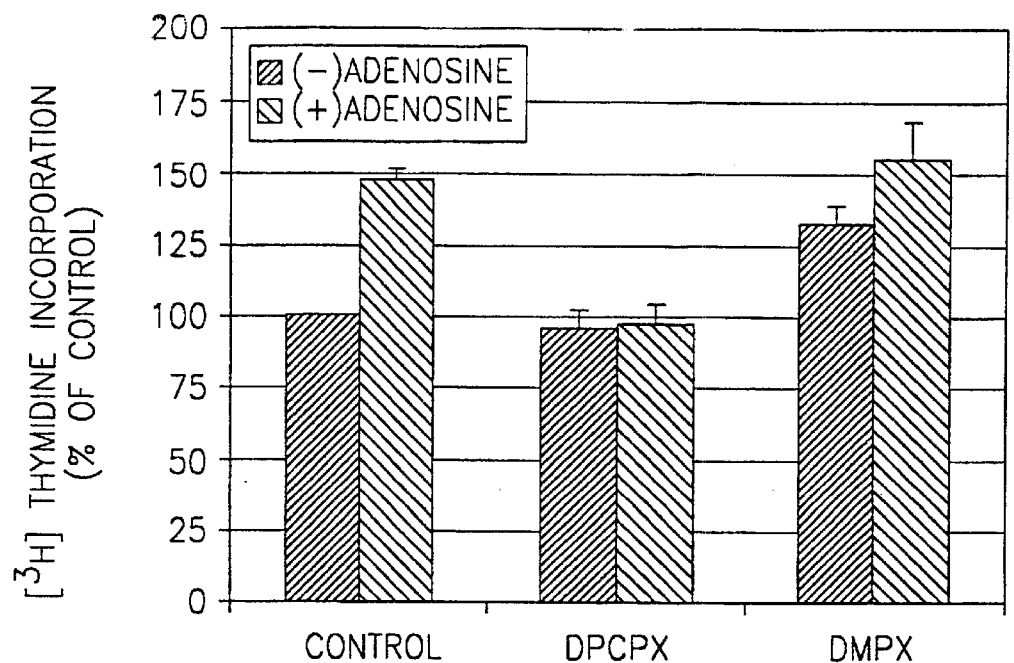
FIG. 1 is a bar graph showing results of an in vitro assay in which proliferation of bone marrow cells was tested without adenosine (dense stripes) and with adenosine (spaced stripes) together with adenosine A$_1$ receptor antagonist (DPCPX) and adenosine A$_2$ receptor antagonist (DMPX) as compared to a control without any additional added drug. The bar graph shows results of a [$^3$H]thymidine incorporation assay.
Figure 2:
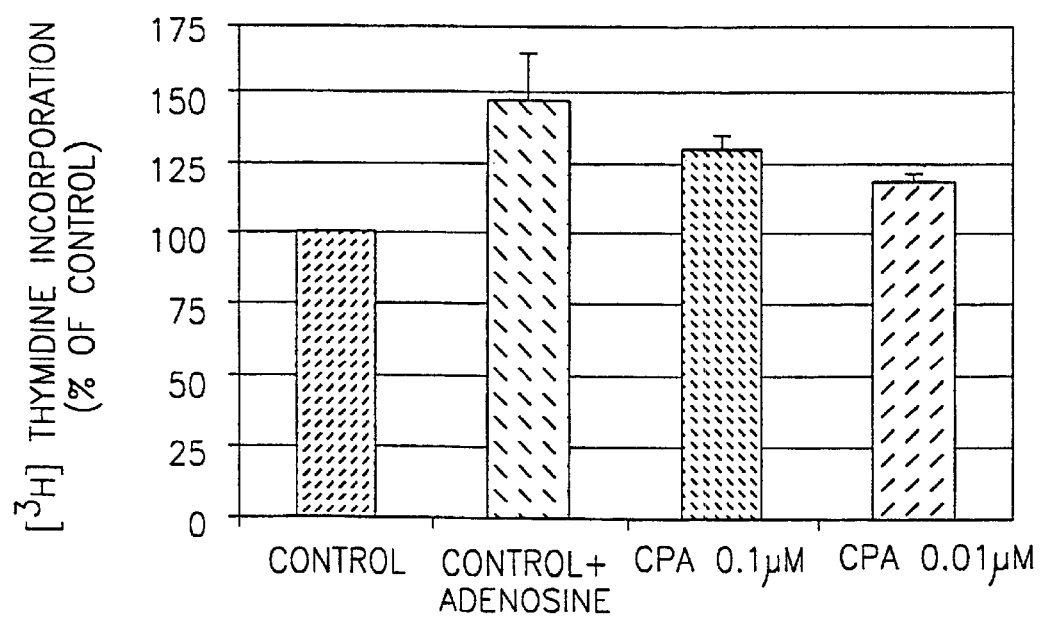
FIG. 2 shows [$^3$H]thymidine incorporation assay of a control bone marrow cell preparation ("control"), in the presence of adenosine ("control+adenosine") and in the presence of two different concentrations of an A1 receptor agonist, ("CPA").

Effect of Adenosine, Adenosine Receptor Antagonists and Agonist on Bone Marrow Cell Proliferation Exposure of bone marrow cells to adenosine at concentrations of 10–50 $\mu$M stimulated $^3$[H]-thymidine incorporation in a concentration dependent manner (Fishman et al.[(4)]). To evaluate which adenosine receptor is responsible for this stimulatory effect, two adenosine receptor antagonists were used, i.e., DPCPX ($A_1$ antagonist) and DMPX ($A_2$ antagonist). The effect of the antagonists on bone marrow cell proliferation was examined with and without adenosine. In the absence of adenosine, the effect of endogenous adenosine which is released by the bone marrow cells and affects the same cells by a paracrine way, was evaluated. DPCPX (0.1 $\mu$M) which block the $A_1$ receptor, significantly reversed the stimulatory effect of adenosine on bone marrow cell proliferation. DMPX (0.1 $\mu$M) given without or with adenosine induced a stimulatory effect on bone marrow cell proliferation (FIG. 1). These results show that the $A_1$ is responsible for the stimulatory effect of adenosine. To confirm this result, CPA, a selective adenosine $A_1$ receptor agonist was added to a culture of bone marrow cells. CPA induced a statistically significant stimulation of bone marrow cell proliferation at concentrations of 0.1 and 0.01 $\mu$M (FIG. 2).

What is claimed is:

1. A method for achieving a therapeutic effect comprising administering to a subject in need an effective amount of a therapeutic agent that is an agonist of the adenosine $A_1$ receptor, the therapeutic effect comprises induction of proliferation of bone marrow cells, wherein said agonist of the adenosine $A_1$ receptor is a compound of general formula (I):

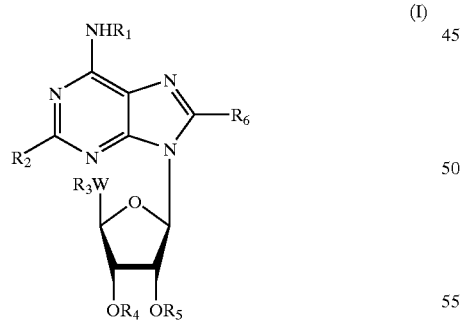

wherein
$R_1$ represents a lower alkyl, substituted or unsubstituted cycloalkyl; a hydroxyl or hydroxyalkyl; a phenyl or lower alkylphenyl, the phenyl or lower alkylphenyl optionally substituted by one or more substituents; —SOR$^c$, —SO$_2$R$^c$, —SO$_3$H, —SO$_2$NR$^a$R$^b$, —OR$^a$, —SR$^a$, —NHSO$_2$R$^c$, —NHCOR$^a$, —NR$^a$R$^b$, or —NHR$^a$CO$_2$R$^b$; wherein
R$^a$ and R$^b$ represent independently a hydrogen, lower alkyl, alkanoyl, amino, phenyl or naphthyl, the alkyl group optionally being substituted with a substituted or unsubstituted phenyl or phenoxy group; or when $R_1$ represents —NR$^a$R$^b$, said R$^a$ and R$^b$ form together with the nitrogen atom a 5- or 6-membered heterocyclic ring optionally containing a second heteroatom selected from the group consisting of oxygen and nitrogen, which second nitrogen heteroatom may optionally be substituted by hydrogen or lower alkyl; or —NR$^a$R$^b$ is a group of general formulae (II) or (III):

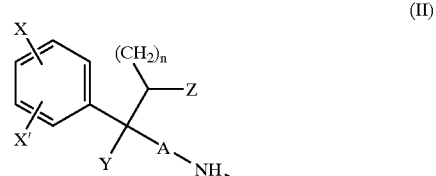

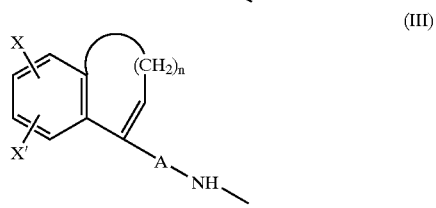

wherein n is an integer from 1 to 4; Z is hydrogen, lower alkyl or hydroxyl; Y is hydrogen, lower alkyl, or OR' where R' is hydrogen, lower alkyl or lower alkanoyl; A is a bond or a lower alkylene; X and X' are each independently hydrogen, lower alkyl, lower alkoxy, hydroxy, lower alkanoyl, nitro, haloalkyl, halogen, amino, mono- or di-lower alkyl amino, or when X and X' are taken together a methylenedioxy group;

R$^c$ represents a lower alkyl; or
$R_1$ represents an epoxide substituent of general formulae (IVa) or (IVb):

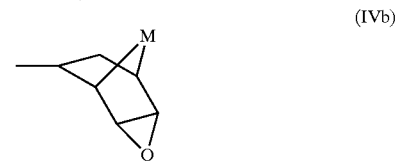

wherein M is a lower alkyl group;
$R_2$ represents hydrogen; halogen; substituted or unsubstituted lower alkyl or alkenyl group; lower haloalkyl or alkenyl; cyano; acetoamido; lower alkoxy; lower alkylamino; NR$^d$R$^e$ where R$^d$ and R$^e$ are independently hydrogen, lower alkyl, phenyl or phenyl substituted by lower alkyl, lower alkoxyl, halogen or haloalkyl; —SR$^f$ where R$^f$ is hydrogen, lower alkyl, lower alkanoyl, benzoyl or phenyl;
W represents the group —OCH$_2$—, —NHCH$_2$—, —SCH$_2$— or —NH(C=O)—;
$R_3$, $R_4$ and $R_5$ represent independently a hydrogen, lower alkyl or lower alkenyl, branched or unbranched $C_1$–$C_{12}$ alkanoyl, benzoyl or benzoyl substituted by lower alkyl, lower alkoxy or halo group; or $R_4$ and $R_5$ form together a 5-membered ring optionally substituted by a lower alkyl or alkenyl; or $R_3$ further represents independently a phosphate, hydrogen phosphate or dihydrogen phosphate, or an alkali metal or ammonium or dialkali or diammonium salt thereof;

$R_6$ represents a hydrogen or halogen atom; or one of the substituents $R_1$ to $R_6$ is a sulfohydrocarbon radical of the formula $R^g$—$SO_3$—$R^{h-}$, wherein $R^g$ represents a group selected from $C_1$–$C_{10}$ alkylenyl, phenylenyl and substituted lower alkyl phenylenyl group and $R^h$ represents a monovalent cation;

wherein when $R_1$ is a substituent of general formula (IVb), the $N^1$-position of the compound of general formula (1) may optionally bear an oxygen atom; and pharmaceutically acceptable salts or solvates of said compound.

2. The method according to claim 1, wherein said therapeutic effect comprises an increase of white blood cell count in the subject's peripheral blood.

3. The method according to claim 1, wherein the treated subject is a cancer patient.

4. The method according to claim 2, wherein the treated subject is a cancer patient whose white blood cell level was reduced as a result of chemotherapy or radiotherapy.

5. The method according to claim 1, wherein said compound is selected from the group consisting of $N^6$-cyclopentyl adenosine (CPA), 2-chloro-CPA (CCPA), and $N^6$-cyclohexyl adenosine (CHA).

6. A method for achieving a therapeutic effect comprising administering to a subject in need an effective amount of a therapeutic agent that is an agonist of an adenosine $A_1$ receptor, the therapeutic effect comprises preventing reduction in level of leukocytes in a subject as a result of a treatment, wherein said agonist of the adenosine $A_1$ receptor is a compound of general formula (I):

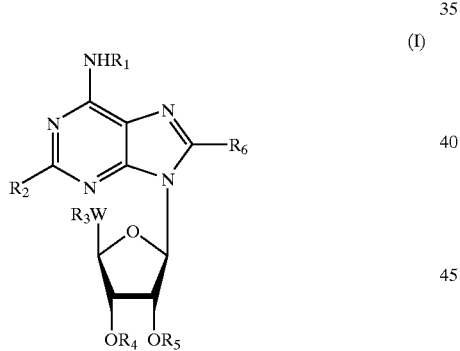

(I)

wherein $R_1$ represents a lower alkyl, substituted or unsubstituted cycloalkyl; a hydroxyl or hydroxyalkyl; a phenyl or lower alkylphenyl, the phenyl and lower alkylphenyl are optionally substituted by one or more substituents; —$SOR^c$, —$SO_2R^c$, —$SO_3H$, —$SO_2NR^aR^b$, —$OR^a$, —$SR^a$, —$NHSO_2R^c$, —$NHCOR^a$, —$NR^aR^b$, or —$NHR^aCO_2R^b$; wherein $R^a$ and $R^b$ represent independently a hydrogen, lower alkyl, alkanoyl, amino, phenyl or naphthyl, the alkyl group optionally being substituted with a substituted or unsubstituted phenyl or phenoxy group; or when $R_1$ represents —$NR^aR^b$, said $R^a$ and $R^b$ form together with the nitrogen atom a 5- or 6-membered heterocyclic ring optionally containing a second heteroatom selected from the group consisting of oxygen and nitrogen, which second nitrogen heteroatom may optionally be further substituted by hydrogen or lower alkyl; or —$NR^aR^b$ is a group of general formulae (II) or (III):

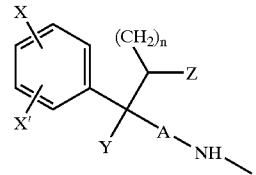

(II)

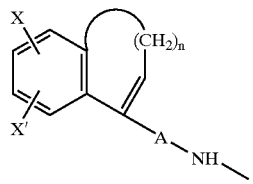

(III)

wherein n is an integer from 1 to 4; Z is hydrogen, lower alkyl or hydroxyl; Y is hydrogen, lower alkyl, or OR' where R' is hydrogen, lower alkyl or lower alkanoyl; A is a bond, a lower alkylene, or a $C_1$–$C_4$ alkenyl; X and X' are each independently hydrogen, lower alkyl, lower alkoxy, hydroxy, lower alkanoyl, nitro, haloalkyl, halogen, amino, mono- or di-lower alkyl amino, or when X and X' are taken together a methylenedioxy group;

$R^c$ represents a lower alkyl; or $R_1$ represents an epoxide substituent of general formulae (IVa) or (IVb):

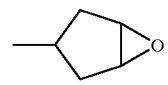

(IVa)

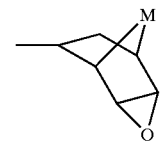

(IVb)

wherein M is a lower alkyl group;

$R_2$ represents hydrogen; halogen; substituted or unsubstituted lower alkyl or alkenyl group; lower haloalkyl or alkenyl; cyano; acetoamido; lower alkoxy; lower alkylamino; $NR^dR^e$ where $R^d$ and $R^e$ are independently hydrogen, lower alkyl, phenyl or phenyl substituted by lower alkyl, lower alkoxy, halogen or haloalkyl or alkoxyl; —$SR^f$ where $R^f$ is hydrogen, lower alkyl, lower alkanoyl, benzoyl or phenyl;

W represents the group —$OCH_2$—, —$NHCH_2$—, —$SCH_2$— or —$NH(C=O)$—;

$R_3$, $R_4$ and $R_5$ represent independently a hydrogen, lower alkyl or lower alkenyl, branched or unbranched $C_1$–$C_{12}$ alkanoyl, benzoyl or benzoyl substituted by lower alkyl, lower alkoxy or halo group; or $R_4$ and $R_5$ form together a 5-membered ring optionally substituted by a lower alkyl or alkenyl; $R_3$ further represents independently a phosphate, hydrogen phosphate or dihydrogen phosphate, or an alkali metal or ammonium or dialkali or diammonium salt thereof;

$R_6$ represents a hydrogen or halogen atom; or one of the substituents $R_1$ to $R_6$ is a sulfohydrocarbon radical of the formula $R^g$—$SO_3$—$R^{h-}$, wherein $R^g$ represents a group selected from $C_1$–$C_{10}$ alkylenyl, phenylenyl and substituted lower alkyl phenylenyl group and $R^h$ represents a monovalent cation;

wherein when $R_1$ is a substituent of general formula (IVb) the $N^1$-position of the compound of general formula (1) may optionally bear an oxygen atom;

and pharmaceutically acceptable salts or solvates of said compound.

7. The method according to claim 6, wherein said leukocytes are neutrophils.

8. The method according to claim 6, wherein said treatment is a drug treatment.

9. The method according to claim 6, wherein said drug is an anti-cancer chemotherapeutic drug or a neuroleptic drug.

10. The method according to claim 6, wherein said compound is selected from the group consisting of $N^6$-cyclopentyl adenosine (CPA), 2-chloro-CPA (CCPA), and $N^6$-cyclohexyl adenosine (CHA).

11. The method according to claim 8, wherein the agonist of the adenosine $A_1$ receptor is administered prior or during a course of administration of the therapeutic drug.

12. The method according to claim 6, wherein said compound is selected from the group consisting of $N^6$-cyclopentyl adenosine (CPA), 2-chloro-CPA (CCPA), and $N^6$-cyclohexyl adenosine (CRA).

13. The method according to claim 1, wherein A is $C_1$–$C_4$ alkenyl, or X or X' are independently trifluoromethyl.

14. The method according to claim 6, wherein X or X' are independently trifluoromethyl.

* * * * *